United States Patent [19]

Wigoda

[11] Patent Number: 4,616,632
[45] Date of Patent: Oct. 14, 1986

[54] LOCK FOR RETRACTOR APPARATUS

[76] Inventor: Luis Wigoda, 841 Washington Ave., Miami Beach, Fla. 33139

[21] Appl. No.: 697,018

[22] Filed: Jan. 31, 1985

[51] Int. Cl.$^4$ ............................................. A61B 17/02
[52] U.S. Cl. ..................................................... 128/20
[58] Field of Search ........................... 128/20; 269/25; 248/281.1, 285, 286, 288.5; 403/15, 31, 55, 56

[56] References Cited

U.S. PATENT DOCUMENTS

| | | | |
|---|---|---|---|
| 3,158,071 | 11/1964 | Gut | 403/56 X |
| 3,491,520 | 1/1970 | Watson | 269/25 X |
| 3,638,973 | 2/1972 | Poletti | 128/20 X |
| 3,858,578 | 1/1975 | Milo | 128/20 |
| 3,915,436 | 10/1975 | Matson | 269/25 X |
| 4,355,631 | 10/1982 | LeVahn | 128/20 |

Primary Examiner—William H. Grieb
Attorney, Agent, or Firm—Harry W. Barron

[57] ABSTRACT

Disclosed herein is a set of retractors which are coupled by releaseable locks to rods on the side of an operating table. A foot pedal is provided to release the locks and allow the retractors to be repositioned easily and with one hand by the doctor while performing the surgery. The foot pedal may utilize hydraulic fluid to lock or release the movement of the retractors. The joint holding the retractors is also rendered free to rotate to properly position the retractors, when the foot pedal is depressed.

18 Claims, 10 Drawing Figures

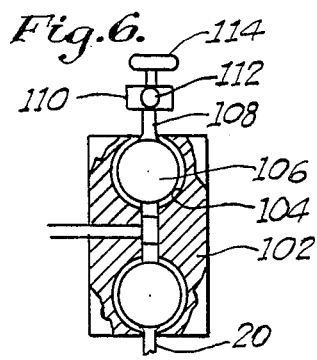
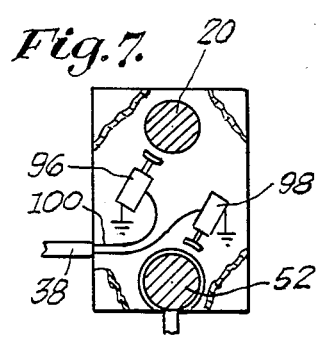
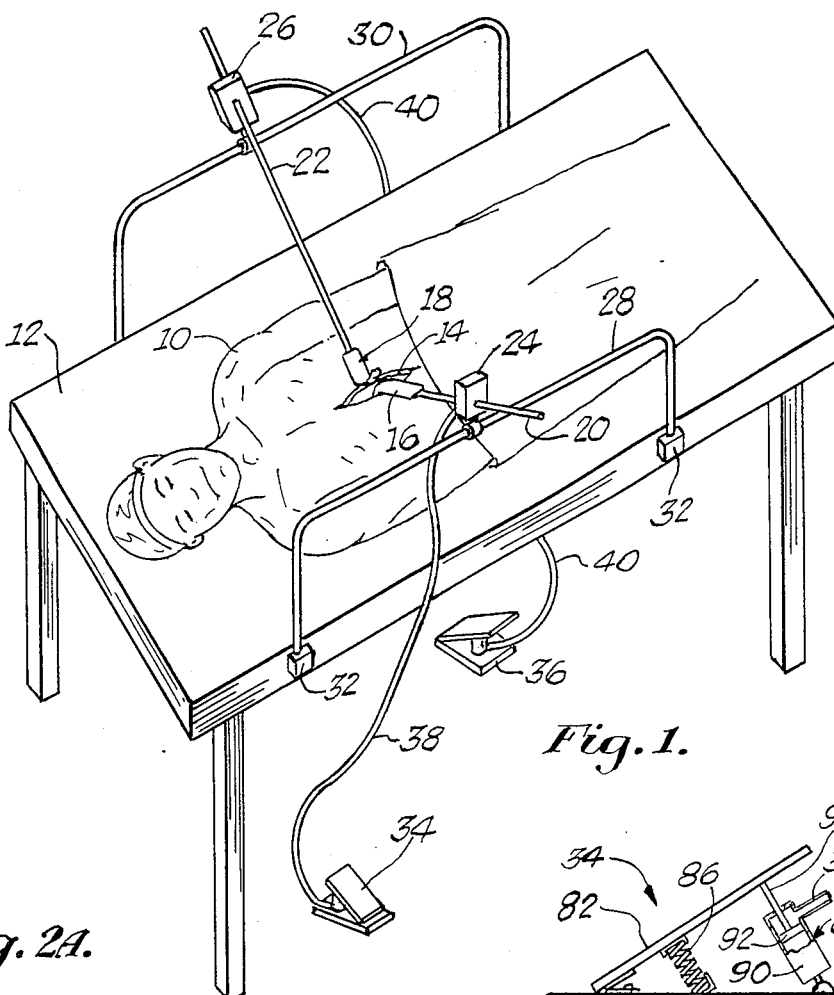
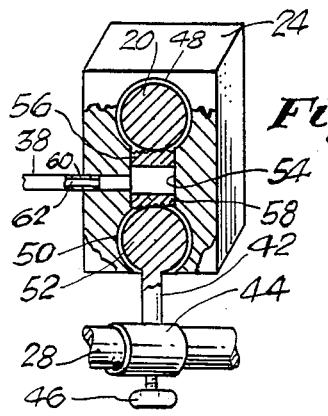
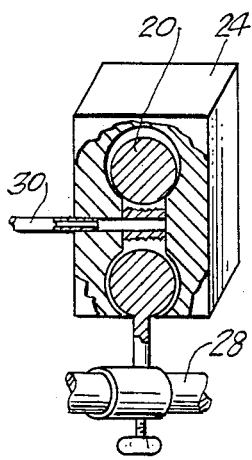
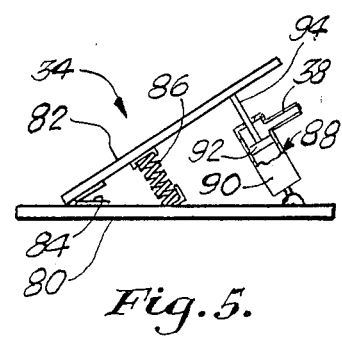
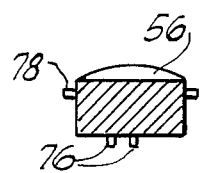
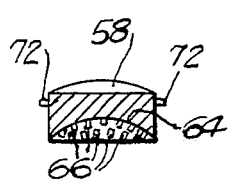
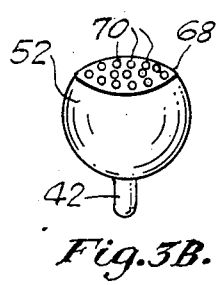
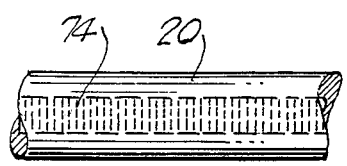

LOCK FOR RETRACTOR APPARATUS

This invention relates to retractor apparatus used during a surgical procedure and more particularly to such apparatus which can be locked or released in repsonse to the actuation of a foot pedal.

For many years retractors have been used during a surgical procedure. Typically at least two retractors are used to pull away different layers of tissue around an incision or body opening to allow the surgeon to work in a desired exposed area. In many instances, two doctors are required, one to hold the retractors and the other to do the acutal surgical procedure. The doctor holding the retractors may become tired very quickly because, in some instances, significant pressure must be applied to the retractor to maintain the desired area clear for the surgeon to proceed.

In surgical applications, mechanical devices have been suggested in the past to replace the second physician holding the retractors. An example of such a mechanical device is described in U.S. Pat. No. 4,355,631 in the name of Bruce A. LeVahn. Other types of devices include those sold by Thompson Surgical Instruments of Barrington, Ill. Typical of these sets of mechanically held retractors is a bar which runs along the side of the operating table. The retractors are connected to rods which can be affixed to mechanisms attached to the bar. The mechanism allows the retractor to be rotated both about and parallel to the bar as well as moved laterally along the bar end towards and away from the patient. Thumb screws or other similar apparatus must be manually loosened to allow the retractor rod to be moved and thereafter tightened when the rod is properly positioned or repositioned. The problem with these types of mechanically held retractors is that during many surgical procedures, it is necessary to readjust the retractors. Sometimes this movement is permanent and other times it will be of a more temporary nature to allow the surgeon to reach a particular area, thereafter the retractor would desirably be placed back in the original position. Because of the manual intervention requirement by the surgeon to loosen the screws on the connectors, the surgeon's concentration may be distracted since he physically must use both hands to loosen the thumb screw and reposition the retractor devices. This means that the surgery itself must stop while the retractors are repositioned. Stopping the surgery is particularly burdensome on the surgeon when it is desired to move retractors for only a short time to reach a specific area within the incision.

It would be more advantageous for the surgeon performing the surgery to have retractors which can be automatically loosened and manually moved without requiring the intervention of both of the surgeons hands. If, for instance, the surgeon were allowed to depress a foot pedal to momentarily free the retractors for movement, he could use one hand to reposition a retractor while still using the other hand to perform the necessary surgical procedure. Thereafter, he could reposition the retractors in the desired position and release the footpedal, thereby locking the retractors.

In accordance with one preferred embodiment of this invention there is provided retractor apparatus for use during a surgical procedure for holding back tissue of a patient undergoing surgery. The apparatus comprises at least one retractor adapted to hold back the tissue and attachment means adapted to attachment relative to an operating platform supporting the patient. In addition, the apparatus includes joint means for affixing the retractor to the attachment means in the position to hold back the tissue. The joint means includes controllable lock means for releasing the retractor for positioning and thereafter locking the positioned retractor and actuated controller means coupled to the lock means for controlling the lock means to release the retractor upon actuation thereof and for controlling the lock means to lock the retractor upon deactuation thereof.

One preferred embodiment of the subject invention is hereafter described with specific reference being made to the following figures, in which:

FIG. 1 shows the foot pedal actuated retractor mechanisms of the subject invention;

FIGS. 2a and 2b show the manner of implementing the locking mechanisms by a hydraulic release and lock;

FIGS. 3a and 3b show the manner in which the locking mechanism operates for the ball joint;

FIGS. 4a and 4b illustrate the manner in which the locking mechanisms operate for the rod attached to the retractor;

FIG. 5 shows the foot pedal apparatus of the subject invention;

FIG. 6 shows an alternate embodiment of the locking apparatus of the subject invention; and FIG. 7 shows another alternate embodiment of locking apparatus of the subject invention.

Referring now to FIG. 1, a patient 10 is shown positioned on an operating table 12. Patient 10 has an incision 14 on his body which typically is made by a surgeon during a surgical procedure. In order to maintain the tissue beneath incision 14 separated so that the surgeon is able to operate within the body at the desired location, a pair of retractors 16 and 18 at the end of retractor rods 20 and 22 are used. The retractor rods 20 and 22 are held by retractor joints 24 and 26 respectively. Each of the joints 24 and 26 are in turn held on rods 28 and 30 which are affixed to the side of operating table 12 by members 32 in a conventional manner. Joints 24 and 26 may alternatively be coupled to mechanisms remote from table 12, such as floor stands or ceiling extensions.

The retractor rods 20 and 22 may slide through joints 24 and 26 to be positioned lengthwise at the appropriate position of incision 14. Joints 24 and 26 slide along rods 28 and 30 respectively until retractors 16 and 18 are properly positioned. Joints 24 and 26 are also tiltable to position retractors 16 and 18 at the proper angle. Thus, by sliding joints 24 and 26 to their proper position along rods 28 and 30 and by tilting joints 24 and 26 and extending retractor rods 20 and 22 to the proper position, the tissue beneath incision 14 may be maintained separated in the manner to allow the surgery to be performed. To be used in surgical application, each of the components heretofore described must be of a material capable of being sterilized, such as stainless steel.

Each of the joints 24 and 26 are respectively coupled to one of the foot controllers 34 and 36 by a controller cable 38 and 40. Foot controllers 34 and 36 may control the locking of joints 24 and 26 either in a hydraulic, electromechanical or mechanical manner. Cable 38 then would be a corresponding hydraulic line, electrical wire or mechanical cable. For purposes of FIG. 1, whenever one of the foot controllers 34 and 36 is depressed, the locking mechanism within the joint 24 or 26 corresponding to that controller is released so that the retractor rod 20 can be moved inward or outward from the joint 24 or 26. In addition, the joint 24 or 26 is able to be tilted or rotated to properly position the retractor within incision 14. Once initially positioned, small movements of retractor 16 or retractor 18 may be accomplished by the surgeon during the middle of a surgical procedure by the surgeon merely depressing one of the foot controllers 34 or 36 and moving the retractor with his free hand.

In FIG. 1, incision 14 is shown in generally the chest portion of patient 10. It should be understood that incision 14 could be anywhere on patient 10 and that retractors 16 and 18 could be used where no incision is required, such as during gynecological surgery.

Referring now to FIGS. 2A and 2B, a hydraulic version of joint 24 is hereafter described. It should be understood that joint 26 would be identical to joint 24 described in FIGS. 2A and 2B. Joint 24 is coupled to rod 28 by a support rod 42 coupled to a slide ring 44 which in turn is secured to rod 28 by a thumb screw 46. Support ring 44 may be moved along rod 28 to the desired position generally perpendicular to that part of incision 14 where retractor 16 is to be positioned. By selecting the rotary position where thumb screw 46 is secured, joint 24 may be tilted towards incision 14 as desired.

Joint 24 is a generally solid material having a cylindrical opening 48 therethrough through which retractor rod 20 is inserted. A second spherical opening 50 is also provided into which a generally spherical ball 52 is positioned. The bottom of spherical ball 52 is connected to support rod 42. Both openings 48 and 50 are slightly larger than retractor rod 20 and ball 52 so that absent a locking action, to be described hereafter, each may slide or rotate within the opening. A hydraulic passage 54 is positioned between cylindrical opening 48 and spherical opening 50. Within hydraulic passage 54 are positioned a pair of hydraulic pistons 56 and 58 associated with respective openings 48 and 50. A second hydraulic passage 60 is further provided from hydraulic passage 54 to a hydraulic fitting 62 to which controller cable 38 is attached. In the hydraulic version shown in FIGS. 2A and 2B, controller cable 38 may be a hydraulic hose.

As long as fluid pressure is maintained within cable 38 and into passage 54 through passage 60, the two pistons 56 and 58 are maintained against retractor rod 20 and ball 52. The manner in which pistons 56 and 58 maintain retractor rod 20 immobile is described in more detail in FIGS. 3A and 3B, and 4A and 4B.

Referring to FIG. 2B, as fluid is moved out of passage 54 through passage 60 and controller cable 38, the pistons 56 and 58 move away from rod 20 and ball 52 to the positions shown in FIG. 2B. In this instance, retractor rod 20 may be moved through the opening 48 towards or away from incision 14. Similarly, joint 24 may be pivoted about ball 52 so that it's angular position may be modified as desired. After the movements of either rod 20 or joint 24 about ball 52 have been accomplished, the hydraulic fluid is forced back into passages 60 and 54 and pistons 56 and 58 return to the locking position shown in FIG. 2A.

Referring now to FIGS. 3A and 3B, the details of piston 58 and ball 52 are shown. Piston 58, shown in FIG. 3A, is cut through the center thereof to show the curvature of the contact face 64. Contact face 64 is generally concave spherical in shape, having approximately the same radius of the radius of ball 52. The outer shape of piston 58 is generally cylindrical in shape having a radius of slightly less than the radius of hydraulic passage 54. Extending down from the radial contact face 64 of piston 58 are a plurality of small extensions or pimples 66. While only two rows of pimples 66 are shown in FIG. 3A, it should be understood that the entire contact face surface includes similar pimples 66. In addition, an "O"-ring 72 is positioned about piston 58 to keep the hydraulic fluid from flowing into contact with ball 52 and out the bottom of joint 24.

In FIG. 3B, ball 52 is shown generally as a sphere connected to support rod 42. Contact surface 68 of ball 52 is positioned opposite to rod 42 and includes a plurality of pimples 70 extending upward therefrom. Pimples 66 and 70 are arranged to mesh within one another so that when piston 58 is moved by hydraulic pressure against contact surface 68 of ball 52, no relative movement between piston 58 and ball 52 can occur. This in turn maintains joint 24 in a fixed position relative to the various movements it can make around ball 52.

Referring now to FIGS. 4A and 4B, piston 56 and retractor rod 20 are shown. Retractor rod 20, shown in FIG. 4B, includes a locking surface 74 having a series of slot openings. Piston 56, shown in FIG. 4A includes a plurality of, for instance two, finger extensions extending from the bottom thereof, which are sized to fit within a corresponding plurality of the slots on locking surface 74. When so engaged, retractor rod 20 is held firmly in a fixed position. Piston 56 also includes an "O"-ring 78 to prevent the hydraulic fluid from getting into the opening 48.

Referring now to FIG. 5, a more detailed view of foot controller 34 is shown. Controller 34 consists of a base 80 and a foot pedal 82 connected to base 80 by a hinge 84. Foot pedal 82 is maintained normally in the position shown by a spring 86. Also coupled between base 80 and foot pedal 82 is a piston and cylinder assembly 88 which consists of a cylinder 90, a piston 92 and a piston rod 94. The hydraulic hose controller cable 38 is coupled to the upper end of cylinder 90 so as to be on the rod side of piston 92. Thus when foot pedal 82 is depressed, piston rod 94 drives piston 92 deeper into cylinder 90 fluid from cable 38 and out from hydraulic passage 54 and opening 60 in FIG. 2A. This, in turn, releases pistons 56 and 58 from engaging retractor rod 20 and ball 52 so that they can be readily moved as previously explained. When foot pedal 82 is released, spring 86 forces foot pedal 82 back to the position shown in FIG. 5. This, in turn, raises piston 92 forcing fluid back into controller cable 38 and into hydraulic passage 54 which moves pistons 56 and 58 to the position shown in FIG. 2A locking retractor rod 20 and ball 52. The amount of fluid in cable 38, passages 54 and 60 and the upper portion of cylinder 90 will determine how far pedal 82 is moved after release. Spring 86 causes a pressure to be applied by piston 91 against this fluid, which pressure is applied throughout the fluid to lock pistons 56 and 58 against rod 20 and ball 52.

Referring now to FIG. 6, an alternate embodiment of a joint 102 is shown. Joint 102 differs from joint 24 in that the cylindrical opening 48 holding rod 20 is replaced by a spherical opening 104 holding a ball 106 similar to ball 52. The stem rod 108 from ball 106 is coupled to a holder 110 for holding a retractor 112 which may be tightened by a thumb screw 114. Joint 102 has the advantage that retractor 112 may be moved with more degrees of freedom than was the case with joint 24.

Referring now to FIG. 7 another alternate embodiment of the foot controlled retractor system is shown in which rod 20 and ball 52 are locked through the use of electric solenoids 96 and 98. The end of the electric solenoids 96 and 98 are similar to the pistons 56 and 58 shown in FIGS. 3A and 4A and the rod 20 and ball 52 are similar to that shown in FIGS. 3B and 4B. Wires 100 extending through controller cable 38 are used to energize solenoids 96 and 98. In FIG. 5, foot pedal 34 would be modified so that when pedal 82 is depressed, short circuit connections energizing wires 100 would be made.

Other types such as mechanical linkages could be utilized to engage or free rod 20 and ball 52. For example, rather than utilizing rod 28 attached to the operating table 12, as shown in FIG. 1, joint 24 or 102 could be attached to one or more extension members or arms from either a fixed floor stand or the ceiling above table 12. The arms could be interlocked by joints to be positioned so that retractors 16 are properly positioned when inserted in joint 24 or 102, at the end of the arms. Such interlocked arms could also be attached to table 12.

What is claimed is:

1. Retractor apparatus for use during a surgical procedure for holding back tissue of a patient undergoing surgery, said apparatus comprising:
    at least one retractor adapted to hold back said tissue;
    attachment means adapted for attachment relative to an operating platform supporting said patient;
    joint means for affixing said retractor to said attachment means in the position to hold back said tissue, said joint means including controllable lock means for releasing said retractor for positioning and thereafter locking said positioned retractor, said retractor being positioned by linear movement through said joint means in a direction away from said attachment means and by rotational movement in a direction about said attachment means; and
    actuated controller means coupled to said lock means for controlling said lock means to release said retractor upon actuation thereof and for controlling said lock means to lock said retractor upon deactuation thereof.

2. The invention according to claim 1 wherein said controllable lock means includes hydraulic means.

3. The invention according to claim 1 wherein said controller means is foot actuated.

4. Retractor apparatus for use during a surgical procedure for holding back tissue of a patient undergoing surgery, said apparatus comprising:
    at least one retractor adapted to hold back said tissue;
    attachment means adapted for attachment relative to an operating platform supporting said patient;
    joint means for affixing said retractor to said attachment means in the position to hold back said tissue, said joint means including controllable lock means for releasing said retractor for positioning and thereafter locking said positioned retractor;
    actuated controller means coupled to said lock means for controlling said lock means to release said retractor upon actuation thereof and for controlling said lock means to lock said retractor upon deactuation thereof;
    said joint means including means to release said retractor for movement in a direction away from said attachment means and in a rotational direction about said attachment means;
    said retractor being connected at the end of rod means, said rod means being lockedly slideably through said joint means; and
    said joint means being coupled to said attachment means by a lockedly rotatable ball joint connection.

5. The invention according to claim 4 wherein said rod means and said ball joint connection are locked in response to a hydraulically actuated piston positioned thereagainst.

6. The invention according to claim 5 wherein said controller means is foot actuated.

7. The invention according to claim 6 wherein said foot actuated controller means includes a hydraulic piston and cylinder assembly for drawing fluid away from said joint means upon actuation thereof.

8. The invention according to claim 7 wherein said foot actuated controller means includes spring means to reset said foot actuated means after actuation.

9. The invention according to claim 6 wherein a hydraulic cylinder is positioned between said rod means and said ball joint connection, a pair of pistons being positioned within said cylinder, and said foot actuated controller is hydraulically coupled to said cylinder at a point between said pair of pistons.

10. The invention according to claim 9 wherein said foot actuated controller means includes a hydraulic piston and cylinder assembly for drawing fluid away from said joint means upon actuation thereof.

11. The invention according to claim 10 wherein said foot actuated controller means includes spring means to reset said foot actuated means after actuation.

12. The invention according to claim 4 wherein said rod means and said ball joint connection are locked in response to an electrically actuated solenoid piston positioned thereagainst.

13. Retractor apparatus for use during a surgical procedure for holding back tissue of a patient undergoing surgery, said apparatus comprising:
    at least one retractor adapted to hold back said tissue;
    attachment means adapted for attachment relative to an operating platform supporting said patient;
    joint means for affixing said retractor to said attachment means in the position to hold back said tissue, said joint means including controllable lock means for releasing said retractor for positioning and thereafter locking said positioned retractor;
    actuated controller means coupled to said lock means for controlling said lock means to release said retractor upon actuation thereof and for controlling said lock means to lock said retractor upon deactuation thereof;
    said joint means including means to release said retractor for movement in a direction away from said attachment means and in a rotational direction about said attachment means; and
    said joint means further including a pair of rotatable ball means, each having a stem extending therefrom, each ball means rotating within said joint means with said stems extending from said joint means, one of said stems being affixed to said retractor means and said other stem being affixed to said attachment means.

14. The invention according to claim 13 wherein said controller means is foot actuated.

15. The invention according to claim 13 wherein both of said ball means are locked in response to a hydraulically actuated piston positioned thereagainst.

16. The invention according to claim 15 wherein said controller means is foot actuated.

17. The invention according to claim 16 wherein said foot actuated controller means includes a hydraulic piston and cylinder assembly for drawing fluid away from said joint means upon actuation thereof.

18. The invention according to claim 17 wherein said foot actuated controller means includes spring means to reset said foot actuated means after actuation.

* * * * *